United States Patent [19]

Vitori et al.

[11] Patent Number: 4,901,730
[45] Date of Patent: Feb. 20, 1990

[54] THERMOGRAPHIC IMAGING ENCLOSURE

[75] Inventors: Ronald J. Vitori, Bethpage; Edward M. Altchek, Riverhead, both of N.Y.

[73] Assignee: New York Chiropractic College, Old Brookville, N.Y.

[21] Appl. No.: 294,819

[22] Filed: Jan. 9, 1989

[51] Int. Cl.⁴ ............................................ A61B 5/00
[52] U.S. Cl. ................................ 128/664; 128/736; 600/21; 374/120; 378/37; 52/239
[58] Field of Search ............... 128/736, 664; 52/63, 52/79.6, 239; 600/21; 374/120, 121; 109/21, 31; 378/37

[56] References Cited

U.S. PATENT DOCUMENTS

| | | | |
|---|---|---|---|
| 3,335,716 | 8/1967 | Alt et al. | 128/664 |
| 4,571,904 | 2/1986 | Kessler et al. | 52/239 |
| 4,635,418 | 1/1987 | Hobgood | 52/239 |
| 4,684,425 | 8/1987 | Bannister | 52/239 |
| 4,738,266 | 4/1988 | Thatcher | 128/664 |

Primary Examiner—Max Hindenburg
Assistant Examiner—K. M. Pfaffle
Attorney, Agent, or Firm—Eliot S. Gerber

[57] ABSTRACT

In a medical thermographic imaging system a patient is examined while standing in a thermo-stable enclosure erected within an examination room. The enclosure is constructed of black natural cloth which is attached to a frame formed of plastic tubular members. The enclosure has an outer vertical wall opposite its entrance to block air currents from blowing through its entrance. The enclosure provides privacy to the disrobed patients.

6 Claims, 2 Drawing Sheets

THERMOGRAPHIC IMAGING ENCLOSURE

BACKGROUND OF THE INVENTION

1. Field of the Invention

The present invention relates to medical systems and more particularly to a projection thermographic imaging system including an air-motion resistant thermo-stable enclosure for the patient.

2. Description of the Related Art

In thermographic imaging an image is obtained of a portion of the human body, in the infra-red frequency band, from the heat produced by the body.

It has been recognized that the heat produced at locations on the body surface may differ, depending on the state of the tissue underlying the skin. For example, in breast cancer detection an area of skin of a breast overlying a tumor will frequently produce more heat than the surrounding area. One method of detecting such differential heat areas is direct contact thermography, in which a sheet of luminescent liquid crystal material responds to temperature gradations at the skin by color changes. An alternative, and generally considered more accurate, system, called projection thermography, produces an image of the thermal radiation from a body portion. The image is produced by an optical system (transducer) which converts the infra-red (thermal) radiation to a visible image. The image may be viewed immediately by a physician, on a screen using a thermograph camera, and may be photographed for later study.

The thermograph camera has a phototube sensitive to infrared radiation (heat) and electronic circuitry to convert the infrared image into signals which may be used to produce a visible image. Sometimes the thermograph camera is connected by a cable to a remote CRT monitor which diplays the visible image.

The infrared radiation which is produced by the human body is very faint. Consequently, the thermograph camera must amplify the infrared image it receives many thousands of times. The thermal emission from the human body, because it is so faint and sensitive, may easily be lost in the ambient heat loss and noise due to clothing worn by the patient, air currents, and rapid temperature changes in the examining room. To eliminate interference from clothing, often the patient disrobes, so he or she is naked, during the thermograph examination. In addition, it is important that the room temperature be kept within a narrow range to prevent artifacts which distort and falsify the image. Such disrobing is embarrassing and uncomfortable to many persons, particularly if they must wait in a cool examining room. If the patient wears a robe, his or her body infrared radiation may be distorted by the folds of the robe.

U.S. Pat. No. 4,548,212 entitled "Apparatus For Thermographic Examinations" uses a liquid crystal sheath applied to a portion of the body and which is flooded with a cooling liquid or gas. In one embodiment, a body portion sheath, called an air tent, is applied over the neck and cooling air is blown into the sheath to cool the skin.

A typical and suitable thermograph camera thermal video system is the Model 7300 "Probeye" available from Hughes. It uses a solid state infrared imaging system employing a mercury cadmium tellwide detector having a spectral range of 2.0 to 5.6 microns.

SUMMARY OF THE INVENTION

In accordance with the present invention, there is provided a system for the acurate production of body portion images using projection thermography. The system is located in a conventional examination room, for example, in a hospital or physician's office. A special purpose thermostable enclosure cloth (tent) is erected in the examination room using plastic tubular frame members and cloth of a black natural tightly woven material (cotton or linen). The enclosure has vertical walls and a top without a bottom wall and has a passageway opening at a right angle to an inner room formed by the vertical walls. The thermograph camera is positioned within the inner room formed by the enclosure to be pointed at the chest (or body portion) of a standing patient. The CRT monitor, and the physician, are outside of the enclosure.

OBJECTIVES AND FEATURES OF THE INVENTION

It is an objective of the present invention to provide an environment for a thermographic system to detect tissue disfunction by producing a visible image from the thermal radiation produced by a patient, in which the patient stands in an area of constant ambient temperature and in which the patient does not feel embarrassment or discomfort often associated with disrobing.

It is a further objective of the present invention to provide such a thermograph system in which there is no distortion or attenuation of the thermal radiation from the patient's body due to clothing or a robe.

It is a further objective of the present invention to provide such a thermographic environment in which there is no distortion or attenuation to disturb the accuracy of the thermograph image and yet there is provide adequate air ventilation and heat exchange with the air of the examination room.

It is a further objective of the present invention to provide such a thermograph system in which the drafts due to movement of the physician, or others, in the examining room do not degrade the thermograph image.

BRIEF DESCRIPTION OF THE DRAWINGS

Other objectives and features of the present invention will be apparent from the following detailed description of a preferred embodiment, taken in conjunction with the accompanying drawings.

In the drawings.

DETAILED DESCRIPTION OF THE PREFERRED EMBODIMENTS

Figure 1:
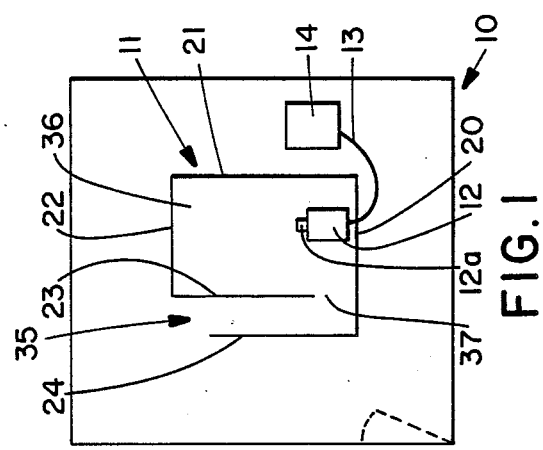
FIG. 1 is a top plan view of the projection thermograph system of the present invention with the roof of the thermo-stable enclosure removed.

As shown in FIG. 1, an examination room 10, in a hospital or physician's office suite, is preferably a room without windows, so that it is relatively thermally stable. The examination room is kept at a constant temperature, for example, 70° F., if necessary, using an electric supplemental heater.

A thermo-stable enclosure 11 (tent) is erected without the room 10. A thermograph camera 12 having lens 12a is positioned within the enclosure 11 and has a cable 13 leading to the CRT monitor 14, which is outside of the enclosure 11. The physician watches the monitor screen and may talk to the patient within the enclosure 11.

Figure 2:
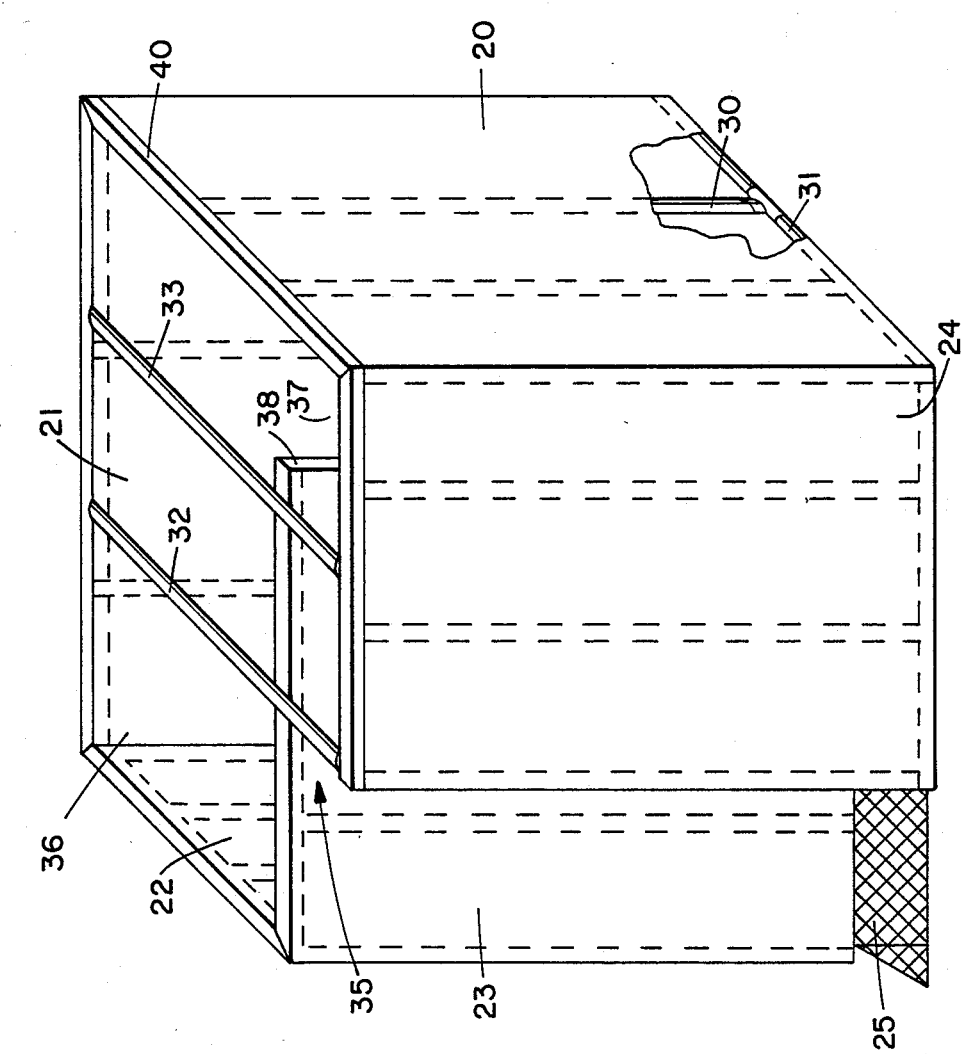
FIG. 2 is a perspective view of a thermo-stable enclosure, without its roof and partially broken-away to show the frame.

The enclosure 11 has five vertical walls 20–24 as shown in FIG. 2. The walls and roof of the enclosure are made of natural cloth, preferably cotton or linen, which is black and closely woven. That type of cloth is less likely to reflect infra-red radiation from the patient's body than artificial polymer cloth or film.

The enclosure 11 is sufficiently large in size so that a person may stand within its walls. The floor is covered by a thick carpet 25 of natural material, such as a thick woolen carpet, which is comfortable to the patient and prevents thermal shock if the room floor is at a colder temperature than the air in the room.

The air in the thermo-stable enclosure 11 is at the same temperature as the air in the room 10 and a supplemental heater is not needed, or desirable, within the enclosure 11. The enclosure 11 provides privacy to the patient, who is completely disrobed, and permits the physician, outside of the tent, to talk to the patient within the enclosure 11.

Figure 3:
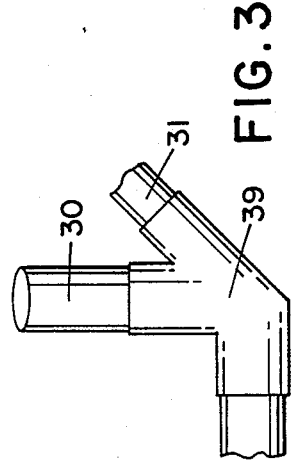
FIG. 3 is an enlarged perspective view of a corner of the frame.

The cloth of the tent consists of two superposed layers with stitching at places; joining the layers to form elongated tunnels. The frame members are non-metal tubular members, preferably plastic resin tubes, which fit within the cloth tunnels. Preferably the frame members are PVC (polyvinlychloride) rigid tubes used for plumbing and are ¾-inch in outside diameter. The frame consists of vertically aligned uprights 30 which are 90 inches in height; plastic tubular "T" joints and corner joints 39 which connect uprights 30 with cross-members 31 as shown in FIG. 3. The frame 29 has preferably sixteen uprights 30. The uprights are connected to the cross-members 31 at the top and bottom of the uprights 30. Two rafters 32, 33 at the top act as supports. The rafters 32, 33 are attached to the cross-members 31 by plastic ties.

Preferably the side wall 20 is 7 feet wide, the side wall 22 is 5 feet wide, the back wall 21 is 10 feet wide, the inner front wall 23 is 7½ feet wide, and the outer front wall 24 is 7 feet wide. The inner front wall 23 and outer front wall 24 form, between them, a 2½-feet-wide passageway 35 through which the patient enters the inner enclosure room 36 through the 2½-feet-wide doorway 37 formed by the end 38 of the inner front wall 23 and the wall 20. Preferably the enclosure is 7.5 feet high. The dimensions may be altered or customized by varying the length of the cross members.

Figure 4:
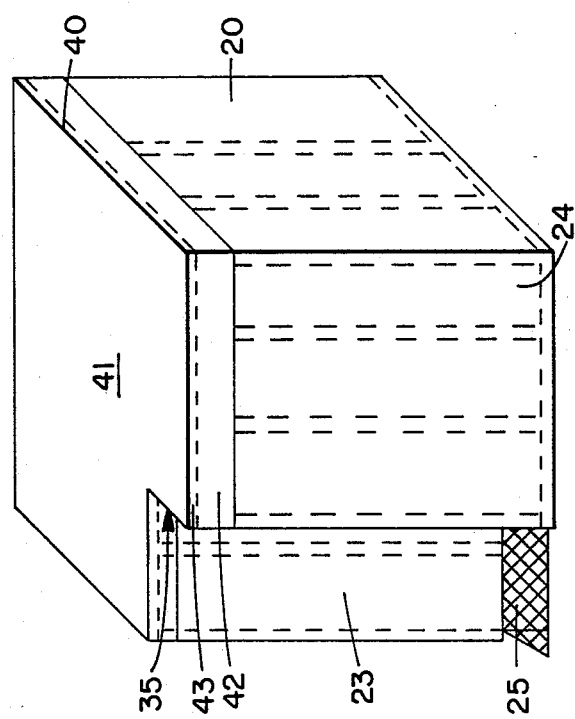
FIG. 4 is a perspective view of the enclosure.

A strip (40) of VELCRO (TM) is secured on the cloth walls 20, 21, 22, 23 and 24, on their outer later, near the top of the wall as shown in FIG. 4. The black cloth roof 41, which is flat on top, has descending flaps 42 on all its sides. Strips 43 of VELCRO (TM) are secured on the inside faces of the flaps 42, which strips 43 are removably secured to the strips 40 to hold the roof 40 to the vertical sidewalls.

The plastic tubular members are preferably held in their joint members only by friction. Alternatively, the plastic tubular members are joined to their joint members by an adhesive, screws, or pins.

As shown in FIG. 1, the camera 12 is mounted against wall 20 so that its lens 12a looks at the patient. The patient stands with his or her back to wall 22 facing the wall 20 and camera lens 12a, during the thermographic examination of the chest or body portion.

The passageway 35 prevents air currents within the room 10 from directly flowing into the inner room 36 and degrading the thermographic image. The patient, within the inner room 36, has privacy and is completely disrobed. The patient may hear instructions from the physician as the walls are cloth. The natural and black cloth material does not reflect heat which may cause artifact (noise).

We claim:

1. An enclosure system for the thermographic imaging of a patient in an examination room, including:
    a plurality of vertical walls of cloth erected within an examination room to form an enclosure and an opening therein, said walls being sufficiently spaced apart so that the patient may stand within said enclosure, and said opening being sufficiently large so that the patient may walk therethrough;
    a vertical wall of cloth connected to said enclosure and extending outwardly therefrom to form with one of said enclosure walls a passageway for the patient to walk therein, said passageway leading to said opening and protecting said opening from direct air currents arising exterior to said enclosure and within said room; and
    an infra-red thermographic camera positioned within said enclosure to take a thermographic image of the patient and a display means to show a visual image of said thermographic image, said display means being exterior of said enclosure and within said examination room.

2. A system as in claim 1 wherein said cloth is a natural cloth material selected from the group of cotton and linen.

3. A system as in claim 2 wherein the cloth is of a non-reflective color.

4. A system as in claim 3 wherein the color of the cloth is black.

5. A system as in claim 1 wherein said enclosure includes a frame of elongated tubular plastic non-heat-conducting members and said walls of cloth are straight-sided walls formed of said cloth stretched on said plastic members.

6. A system as in claim 1 and further including a cloth roof covering said enclosure.

* * * * *